United States Patent [19]

Ferentchak et al.

[11] Patent Number: 4,818,522

[45] Date of Patent: Apr. 4, 1989

[54] ENCAPSULATION OF ADJUVANTS WITHIN ANTIPERSPIRANT ACTIVES

[75] Inventors: Rudolph Ferentchak, New Providence; James F. Kozischek, Belvidere, both of N.J.

[73] Assignee: Reheis, Inc., Berkeley Heights, N.J.

[21] Appl. No.: 96,588

[22] Filed: Sep. 14, 1987

[51] Int. Cl.$^4$ ............................................... A61K 7/34
[52] U.S. Cl. ........................................ 424/66; 424/65; 424/67; 424/68
[58] Field of Search ......................... 424/65, 66, 67, 68

[56] References Cited

U.S. PATENT DOCUMENTS

| | | | |
|---|---|---|---|
| 3,091,156 | 5/1963 | Wurzburg et al. | 167/42 |
| 3,201,353 | 8/1965 | Corben | 252/316 |
| 3,691,271 | 9/1972 | Charie et al. | 424/28 |
| 3,886,125 | 5/1975 | Chromecek | 260/78.3 UA |
| 3,966,902 | 6/1976 | Chromecek | 424/59 |
| 3,979,510 | 9/1976 | Rubino | 424/66 X |
| 4,089,120 | 5/1978 | Kozischek | 34/12 |
| 4,147,766 | 4/1979 | Kozischek | 424/14 |
| 4,278,206 | 7/1981 | Prussin | 239/327 |
| 4,359,456 | 11/1982 | Gosling et al. | 423/462 X |
| 4,364,515 | 12/1982 | Prussin | 239/8 |
| 4,430,155 | 2/1984 | Kozischek et al. | 159/45 |
| 4,579,779 | 4/1986 | Ohno | 428/402.2 |
| 4,605,554 | 8/1986 | Prussin et al. | 424/66 |

Primary Examiner—W. J. Shine
Attorney, Agent, or Firm—Panitch Schwarze Jacobs & Nadel

[57] ABSTRACT

Antiperspirant formulations are provided in which water-immiscible adjuvants are encapsulated in thick-walled, hollow, substantially spherical particles of antiperspirant active, which is preferably a water-soluble compound or complex of a polyvalent metal or metals. The thick-walled particles resist rupture during normal handling and application of the antiperspirant formulation and provide slow release of the encapsulated adjuvant when the antiperspirant shell dissolves in perspiration. The adjuvant may be a fragrance, an antibacterial, antimicrobial or antifungal agent, a deodorant, or other dermatological preparation. The encapsulation is accomplished by emulsifying the adjuvant in an aqueous solution of the antiperspirant active, and spray drying the material in such a manner as to produce thick-walled, spherical particles with the liquid adjuvant in the hollow centers.

20 Claims, No Drawings

1

ENCAPSULATION OF ADJUVANTS WITHIN ANTIPERSPIRANT ACTIVES

FIELD OF THE INVENTION

The present invention relates to antiperspirant compositions or formulations containing adjuvants in encapsulated form. More particularly, the invention relates to the encapsulation of water-immiscible adjuvants within thick-walled shells of an antiperspirant active material.

BACKGROUND OF THE INVENTION

It has been known for many years to provide for the controlled release of various substances ranging from inks to pesticides to fragrances, by encapsulating the desired substance in a matrix or shell of another material, such as a polymer, which is later disintegrated to release the desired substance, either by dissolving the encapsulating material slowly in the environment or by rupturing the encapsulating material by friction or other force during application or use of the substance. As a result, the encapsulated substance is protected during shipping, storing, handling, and sometimes even during application, so that the substance may be released in a slow or controlled manner.

Various methods are also known for encapsulating substances for controlled release. Probably the most commonly used techniques are spray drying and coacervation. In both of these methods a polymeric or similar matrix material, such as a gum, gelatin or porous cellular material, must be provided to contain or incorporate the substance desired to be released. Generally, this encapsulating material is an inert, biodegradable substance, since it will serve no useful purpose after the controlled release is completed.

The patent literature is replete with examples of encapsulated materials, particularly fragrances, perfumes, flavoring agents, pharmaceuticals and cosmetics, including antiperspirants and deodorants. However, in each case, it is necessary to use an extraneous material as at least a part of the encapsulating agent, and applicants are not aware of the prior use of the primary active ingredient as the sole encapsulating agent without the necessity of using extraneous materials to form the encapsulating shell.

For example, U.S. Pat. Nos. 3,886,125 and 3,966,902 of Chromecek disclose the use of polymer complexes containing aluminum, zinc or zirconium metal in complex bound form for entrapping active agents such as medicaments, fragrances, pesticides, antibacterials and like substances. While the aluminum, zinc or zirconium compounds used in the polymer complexes may be ones which have antiperspirant activity, no claims of such activity are made for the complexes, and these metal complex structures are used to inhibit the gelling of the reaction system which requires the polymerization of an organic monomer to form the encapsulating material. Moreover, Chromecek contemplates encapsulating an antiperspirant active aluminum complex within the polymer complex.

U.S. Pat. No. 3,091,567 of Wurzburg, et al. describes a method of emulsifying a flavoring oil or perfume in a solution containing an aluminum sulfate starch derivative. The emulsion is then spray dried to yield free-flowing particles which permit a gradual release of the perfume encapsulated in the particles. While the polyvalent metal salts used to form the starch derivatives may include salts used as antiperspirant actives, no antiperspirant activity is attributed to the derivatives, and the derivatives form water-repellent films.

U.S. Pat. No. 3,691,271 of Charle, et al. discloses the encapsulation of a deodorant within a particle shell such as gelatin, cellulose or polyvinyl alcohol. The deodorant is released as perspiration dissolves or permeates the particle shell. No antiperspirant activity is disclosed or claimed.

U.S. Pat. No. 4,579,779 of Ohno describes a method of encapsulating organic liquids such as fragrances in hollow particles of silica, while U.S. Pat. No. 3,201,353 of Corben describes a method for encapsulating a water-immiscible material within a gelatin complex containing a water-soluble zirconyl salt. The water-immiscible liquid may be a flavoring agent or pharmaceutical, for example.

U.S. Pat. Nos. 4,605,554; 4,364,515 and 4,278,206 of AE Development Corporation describe hydrophobic metal oxides which may contain an antiperspirant or similar material which encapsulates discrete water globules which are released when the metal oxide particles are subjected to high shear mixing, such as during roll-on application of the antiperspirant product.

BRIEF SUMMARY OF THE INVENTION

According to the invention, water-immiscible components which are used in antiperspirant formulations are encapsulated in thick-walled, hollow, substantially spherical particles of the antiperspirant active ingredient which is generally a water-soluble compound or complex of a polyvalent metal or metals. The walls of the antiperspirant particles are sufficiently thick to substantially resist rupture during normal handling and application of the antiperspirant formulation to the human axilla, so that leakage or release of the water-immiscible component is substantially prevented until the antiperspirant shell dissolves in water, particularly perspiration. The water-immiscible component may be a fragrance, an antibacterial, antimicrobial or antifungal agent, a deodorant, an emollient or other dermatological preparation, or other similar adjuvant useful in antiperspirant formulations.

According to the method of the invention, the encapsulation of the water-immiscible component is accomplished by emulsifying the water-immiscible component in an aqueous solution of the antiperspirant active, and spray drying the resulting material, preferably by diffusion of the material through small pores into a stream of heated air, the pores having nominal diameters smaller than the shells of antiperspirant active to be produced. Preferably, the water-immiscible component is a liquid such as an oil, solution or colloidal dispersion which may be emulsified to form an oil-in-water emulsion.

DETAILED DESCRIPTION OF THE PREFERRED EMBODIMENTS

Apparatus and methods are known which can produce thick-walled, essentially spherical particles of antiperspirant materials, such as aluminum, zirconium, zinc and magnesium compounds and complexes, with particle size distributions predominantly in the 10 to 74 micron range. Such methods and apparatus are described in U.S. Pat. Nos. 4,089,120; 4,147,766 and 4,430,155, all assigned to the same assignee as the present invention. The process described in the first two of these patents comprises providing a solution containing the materials from which the particles are made, diffusing the solution through small pores by centrifugal force such that the resulting solution droplets have a diameter greater than the pore diameter, and drying said solution droplets in a stream of heated air. The apparatus described in the first two of these patents comprises a centrifugal atomizer having a porous sintered metal filter ring which is rotated inside a spray drying chamber.

The process of U.S. Pat. No. 4,430,155 comprises providing a solution containing the materials from which the particles are made, dispersing the solution from a central source outwardly along a plurality of radially disposed bristles by centrifugal force to form discrete liquid droplets, and drying the droplets in a stream of heated air to form the particles after the droplets leave the free ends of the bristles. The apparatus of that patent comprises a centrifugal atomizer having a plurality of radially outwardly extending bristles extending from fluid outlets from a generally centrally located solution source, the atomizer being rotated in a spray drying chamber.

It has now been discovered that the above technology for producing thick-walled particles of antiperspirant materials can be used to encapsulate adjuvants which are desired to be protected or preserved during storage, shipping and handling and/or are desired to be released in a slow or controlled manner during and after application and use of the antiperspirant formulation. For example, adjuvants which are particularly volatile or are rapidly absorbed by the skin or clothing may have more prolonged effect by being released over a period of time as the antiperspirant particles are dissolved by perspiration or other body moisture.

The solution from which the thick-walled particles of antiperspirant material are produced may be selected from any of a wide variety of known antiperspirant ingredients, including but not limited to basic aluminum compounds, basic aluminum-zirconium complexes, zinc complexes, other acidic salts and complexes of polyvalent metals and mixtures thereof. Although particular compounds within the broad classes just described are known to those skilled in the antiperspirant manufacturing art, the following more specific compositions are examples of the above-named classes of compounds.

The basic aluminum halides are examples of basic aluminum compounds suitable for use in the present invention. A representative formula is:

$$Al_n(OH)_xA_y \bullet XH_2O$$

wherein $x$ and $y$ need not be integers, but $x+y=3n$, $X$ is a quantity from 2 to 4 which need not be an integer, and A is chlorine, bromine, iodine or mixtures thereof. Compounds within this general formula include the 5/6 basic aluminum halides which have the formula $[Al_2(OH)_5A]$ and the 2/3 basic halides $[Al(OH)_2A]$. For convenience, brackets are used to enclose groups of chemical elements which are not necessarily all of the elements of the molecular structure, and do not mean to exclude $H_2O$ groups.

A widely used antiperspirant complex is aluminum chlorhydroxide or 5/6 basic aluminum chloride which is commercially available from Reheis Chemical Company, Inc. under the trademark "CHLORHYDROL." Many other antiperspirant materials and additives useful in the present invention will be apparent to those of ordinary skill in the art.

The above compounds may be formed in an aqueous solution which is delivered to the atomizer. The aqueous solution contains water or other diluent to enable it to readily diffuse. Typically, a 50% by weight aqueous solution of the compounds has been found satisfactory, but if still lower viscosity is desired, the solution may be heated or may be diluted with water or alcohol to, for example, 25% by weight of the compound in the solution. It is preferred that the solution should be a true solution, but antiperspirant actives which form emulsions or colloidal dispersions in water are suitable, and it will be understood that the term "aqueous solution" or "water soluble" as used herein is intended to cover aqueous emulsions or aqueous colloidal dispersions, as well.

The water-immiscible adjuvants which may be encapsulated according to the present invention are generally oily, organic liquids which are soluble in organic solvents such as ethanol, but are not soluble to any appreciable degree in water. The liquid may contain dissolved solids or colloidally dispersed solids, but mere suspensions are generally not suitable for use in the present invention. Stated otherwise, any adjuvant useful in antiperspirant formulations which is emulsifiable in water or aqueous medium may be encapsulated according to the present invention.

Examples of adjuvants which are particularly desirable for encapsulation in antiperspirant actives include fragrances, antibacterials (including bacteriostats), antimicrobials, antifungals, deodorants, emollients and other dermatological preparations such as moisturizers and skin conditioners. Other types of pharmaceuticals or medicinal agents may also be desirable for incorporation in the antiperspirant particles. The invention is most advantageous for use with volatile adjuvants which are rapidly lost from conventional antiperspirant formulations during handling, storage, shipping, application and use.

For example, it is common to experience a rather strong perfume scent upon initial application of an antiperspirant to the human axilla. However, the scent rapidly disappears and may be imperceptible within an hour or two. An important purpose of the present invention is to securely encapsulate fragrances and other adjuvants in a manner which will minimize the loss of volatiles through capsule breakage, diffusion, etc. so that the adjuvant is released over a period of time as the antiperspirant active slowly dissolves in perspiration.

In order to encapsulate the adjuvant in the antiperspirant active, the adjuvant must be emulsified (not merely suspended) in the aqueous solution of the antiperspirant active. In the case of oily organic liquid adjuvants, the adjuvant should form an oil-in-water emulsion with the aqueous antiperspirant solution. The manner of emulsification of the adjuvant will obviously vary considerably depending upon the particular type of adjuvant to be emulsified.

The particular emulsifying agent to be used is not critical, so long as a stable, spray dryable material is formed and the emulsifying agent does not adversely react with either the adjuvant or the antiperspirant active. Suitable emulsifying agents will be evident to those skilled in the art depending upon the adjuvant to be emulsified. They generally comprise wetting agents and surfactants. Examples of suitable emulsifying agents for use alone or in various combinations in antiperspirant solutions include, but are not limited to, non-ionic emulsifiers such as fatty acid partial esters of polyols or polyol anhydrides, and polyoxyethylene derivatives of fatty acid partial esters of sorbitol anhydrides. These general purpose emulsifiers are available commercially, for example, from ICI Americas, Inc. under the trademarks "ARLACEL" and "TWEEN," respectively.

Spray drying machines conventionally used in the production of powders from solutions include those made by Niro Atomizer, Bowen Engineering, Inc. and Anhydro Corp. In conventional spray drying processes used in the spray drying of antiperspirants, these spray dryers are typically provided with centrifugal atomizers in the form of spinning plate distributors in which the feed solution is supplied to the underside of the spinning plate and spun off the rounded or sharp edges of the plate by centrifugal force.

While virtually any of the spray dryers of the prior art may be used in the production of antiperspirant particles of the present invention, the atomization of the feed liquid in the spray drying chamber according to the invention is preferably carried out by centrifugal atomization of the type described and claimed in our prior U.S. Pat. Nos. 4,089,120 and 4,147,766, the disclosures of which are incorporated herein by reference. As described above, such atomization consists of diffusing a feed liquid through small pores, particularly the pores of a porous sintered metal filter, by centrifugal force, with the pores having a nominal diameter smaller than that of the desired particles, preferably a nominal pore size of about 20 microns.

Antiperspirant powders of the present invention produced by porous metal atomization with a nominal pore size of about 20 microns have a particle size distribution predominantly in the range of about 10 to 74 microns and a particle density of about 1.65 to 1.75 gm/cc. More particularly, the particles have an average particle diameter of about 30 microns, with at least 90% of the particle diameters falling in the range between 10 and 74 microns, and preferably 95% or more of the particle diameters falling within this range.

Alternatively, the atomization of the feed liquid may be carried out using a wire or bristle atomizer of the type described in our U.S. Pat. No. 4,430,155 to produce the necessary thick-walled particles. However, two-fluid atomization and conventional spinning disc atomization produce particles which fail the alcohol test described in Example I below.

Since our prior patents it has been found that particle size is more a function of centrifugal acceleration (force) than centrifugal or peripheral speed--if the speed and force are increased, the fines become too high, and if the speed and force are reduced, the particles become too large and wet. According to the invention the centrifugal atomization occurs at a centrifugal acceleration of at least 175,000 ft/sec/sec and preferably greater than about 300,000 ft/sec/sec.

The antiperspirant particles produced are hollow, thick-walled, essentially spherical particles in which the walls consist essentially of antiperspirant active, and the hollow centers are predominantly or totally filled with the water-immiscible adjuvant, including its emulsifier which is generally a low volatility liquid. Under microscopic examination, the adjuvant and emulsifier generally appear as a cloudy liquid entrapped in the center of the particle. Depending upon how well the immiscible adjuvant is emulsified, the adjuvant may be present within the particle as a single drop or as many dispersed drops. Since the particle walls or shells consist essentially of antiperspirant active, there is no extraneous material which could dilute or interfere with antiperspirant efficacy.

The encapsulated adjuvant(s) may be present in the antiperspirant formulations of the invention in a wide range of concentrations up to a total amount of about six weight percent or more based upon the total weight of the dried particles. In general, the amount of encapsulated adjuvant necessary to be included in the formulations may be significantly smaller than amounts required in prior art antiperspirant formulations with non-encapsulated adjuvants, due to the reduction of losses of volatiles. While it may be possible to somewhat increase the persistence time of an adjuvant in conventional non-encapsulated formulations by simply increasing the amount of adjuvant, the initial potency of the adjuvant upon application may be overpowering and even offensively strong compared to slow release encapsulated adjuvants.

It should be understood also that more than one of the adjuvants of the conventional antiperspirant formulations may be encapsulated in the antiperspirant active according to the present invention, while other adjuvants or additional amounts of the encapsulated adjuvant may be added later in the usual formulations. For example, it may be desirable to include in the formulation both encapsulated and non-encapsulated fragrance so that there will be an initial scent before perspiration begins dissolving the particle shells.

The invention will now be illustrated in more detail by reference to the following specific, non-limiting examples:

EXAMPLE I

To 1860 grams of a 50% CHLORHYDROL solution was added 100 grams of Tween 20 emulsifier from ICI Americas, Inc. The emulsifier was mixed with the CHLORHYDROL solution for five minutes using an overhead stirrer until well blended. 40 grams of fragrance (Alpine Ban type no. 104-666) was then added to the above mixture and mixed for about 10 minutes to obtain thorough emulsification of the fragrance.

The above feed material was spray dried in a Bowen laboratory spray dryer (type BLSA) at a feed rate of 50 ml per minute and an outlet temperature of 90 degrees centigrade, using a porous metal atomizer according to U.S. Pat. No. 4,089,120. The resulting powder contained about 4.0 weight percent fragrance based on the weight of the dried particles.

To test for encapsulation, the resulting powder was placed in SDA-40 alcohol (in which the powder is insoluble). The only odor was that of the alcohol, and no fragrance could be smelled. When deionized water was added to this alcohol/powder suspension, the particle shells dissolved immediately, and the fragrance could be smelled distinctly.

The same powder was then formulated in an aerosol base containing 40% by weight of the antiperspirant powder, 53.6% by weight isopropyl myristate, 3.2% Bentone 38 and 3.2% SDA-40 alcohol, and 0.4% non-encapsulated fragrance (Alpine Ban type no. 104-666). A similar aerosol formulation was prepared from Reheis MACROSPHERICAL 95 without encapsulation, but with the same amount of fragrance simply added to the formulation after spray drying. Cans of each formulation were provided to an in-house test panel for comparison and evaluation according to the protocol of Table I. Due to valve clogging problems (not related to the encapsulation process), the quantity of data obtained was less than planned for. However, the consensus of the data obtained overwhelmingly demonstrated that the fragrance emitted by the control formulation had essentially dissipated within two hours after application. On the other hand, the fragrance emitted by the encapsulated product lasted a minimum of four hours in all cases, in most cases as long as eight hours, and in a few cases up to twelve hours.

The above ingredients were combined and spray dried in the same manner as in Example II. Batches spray dried at outlet temperatures of 95° C. and 110° C., respectively, yielded good powders which passed the alcohol test of Example I. Similar batches containing only 2 percent ARLACEL and 91.9 percent CHLORHYDROL yielded moist powders.

TABLE I

| Fragrance Strength Comparative Test | | | | |
|---|---|---|---|---|
| MON. | TUES. | WED. | THURS. | FRI. |
| Right arm–Left arm | Right arm–Left arm | Right arm–Left arm | Right arm–Left arm | Right arm–Left arm |
| Initial | | | | |
| 2 hr. | | | | |
| 4 hr. | | | | |
| 8 hr. | | | | |

Instructions to panel participants:
(1.) Apply antiperspirant in your normal manner.
(2.) Insure that both applications (cans labeled "for right arm" and "for left arm") are applied in a duplicate manner.
(3.) Wait two minutes, then check by sniffing for initial fragrance level (level to be recorded as none, weak, moderate or strong).
(4.) Subsequent odor checks made by sniffing through garments you are wearing.

NOTE!
Other body fragrance (excluding after-shave lotion) should not be used during this testing period.

EXAMPLE II

An antiperspirant formulation was made containing the following ingredients:

| Ingredient | Weight Percent |
|---|---|
| CHLORHYDROL (50% solution) | 89.9 |
| TWEEN 20 | 5.0 |
| ARLACEL 165 | 4.0 |
| Vitamin E | 1.0 |
| Alpine fragrance (Ban type #104-666) | 0.1 |
| | 100.0 |

The TWEEN 20 was added to the CHLORHYDROL with overhead stirring, and the mixture was heated for 65° C. The ARLACEL 165 was heated until melted and then added to the above mixture with stirring. The Vitamin E and Alpine fragrance were then added in order with good agitation, and stirring was continued while the mixture was cooled to room temperature.

The resulting mixture was spray dried as in Example I at a feed rate of 50-60 ml. per minute. One batch was spray dried at an outlet temperature of 90-95° C. and another at an outlet temperature of about 110° C. Both batches show good misting, fluid powders with low moisture, some spheres were broken in the second batch. The resulting powders of both batches passed the alcohol test of Example I. Three other batches with only 2% ARLACEL yielded moist powders regardless of whether run at outlet temperatures of 90-95° C., 110-120° C. or 140° C.

EXAMPLE III

An antiperspirant formulation was made containing the following ingredients:

| Ingredient | Weight Percent |
|---|---|
| CHLORHYDROL (50% solution) | 89.9 |
| TWEEN 20 | 5.0 |
| ARLACEL 165 | 4.0 |
| Aloe vera | 1.0 |
| Unisex fragrance (Bush Boake Allen #858832) | 0.1 |
| | 100.0 |

The present invention may be embodied in other specific forms without departing from the spirit or essential attributes thereof and accordingly, reference should be made to the appended claims, rather than to the foregoing specification as indicating the scope of the invention.

We claim:

1. An antiperspirant composition comprising thick-walled, hollow, essentially spherical particles, the walls of said particles consisting essentially of a water soluble compound or complex of a polyvalent metal having antiperspirant efficacy and the hollow interior of said particles being at least partially filled with a water-immiscible component of said antiperspirant composition.

2. An antiperspirant composition according to claim 1 wherein the walls of said particles are sufficiently thick to substantially resist rupture of said walls and leakage of said water-immiscible component during normal handling and application of said composition to the human axilla.

3. An antiperspirant composition according to claim 1 wherein the walls of said particles are sufficiently thick that said water-immiscible component is released substantially only upon dissolution of said walls in water.

4. An antiperspirant composition according to claim 1 wherein said polyvalent metal is selected from the group consisting of aluminum, zirconium, zinc, and magnesium.

5. An antiperspirant composition according to claim 4 wherein said particle walls consist essentially of an aluminum chlorhydrate compound or complex.

6. An antiperspirant composition according to claim 4 wherein said particle walls consist essentially of an aluminum-zirconium complex.

7. An antiperspirant composition according to claim 1 wherein said water-immiscible component is selected from the group consisting of fragrances, antibacterials, antimicrobials, antifungals, deodorants, dermatological preparations and emollients.

8. An antiperspirant composition according to claim 1 wherein said particles have diameters predominantly in the range of about 10 to 74 microns.

9. An antiperspirant composition according to claim 1 wherein said particles have a particle density of about 1.65 gm/cc to 1.75 gm/cc.

10. An antiperspirant composition according to claim 1 wherein said water-immiscible component is present in an amount up to about six weight percent based upon the total weight of the particles.

11. A method of encapsulating a water-immiscible component of an antiperspirant composition within thick-walled, essentially spherical particle shells consisting essentially of a water soluble antiperspirant active, comprising the steps of providing an aqueous solution of the antiperspirant active, emulsifying said water-immiscible component in said solution, and spray drying the resulting material by diffusing the material through small pores into a stream of heated air, said pores having nominal diameters smaller than the shells of antiperspirant active formed thereby.

12. A method according to claim 11 wherein said antiperspirant active is a compound or complex of a polyvalent metal.

13. A method according to claim 12 wherein said polyvalent metal is selected from the group consisting of aluminum, zirconium, zinc, and magnesium.

14. A method according to claim 11 wherein said water-immiscible component is selected from the group consisting of fragrances, antibacterials, antimicrobial, antifungals, deodorants, emollients, and dermatological preparations.

15. A method according to claim 11 wherein said emulsification step comprises forming an oil-in-water emulsion.

16. A method according to claim 11 wherein said water-immiscible component is a liquid.

17. A method according to claim 16 wherein said liquid is selected from the group consisting of oils, solutions and colloidal dispersions.

18. A method according to claim 17 wherein said liquid is a fragrance oil.

19. A method according to claim 11 wherein said spray drying step includes passing said material through a centrifugal atomizer comprising a peripheral ring of porous sintered metal.

20. A method according to claim 19 wherein said porous sintered metal ring has a nominal pore size of about 20 microns which produces macrospherical particles having an average diameter of about 30 microns.

* * * * *